(12) United States Patent
Thieme-Marti et al.

(10) Patent No.: US 12,097,386 B2
(45) Date of Patent: Sep. 24, 2024

(54) PATH PLANNING FOR RADIATION TREATMENT

(71) Applicant: Varian Medical Systems International AG, Cham (CH)

(72) Inventors: Stefan Thieme-Marti, Windisch (CH); Jennifer Kieselmann, Aargau (CH)

(73) Assignee: Siemens Healthineers International AG, Steinhausen (CH)

( * ) Notice: Subject to any disclaimer, the term of this patent is extended or adjusted under 35 U.S.C. 154(b) by 784 days.

(21) Appl. No.: 17/208,898

(22) Filed: Mar. 22, 2021

(65) Prior Publication Data
US 2022/0296921 A1 Sep. 22, 2022

(51) Int. Cl.
*A61N 5/10* (2006.01)
*A61B 6/00* (2024.01)
*G16H 20/40* (2018.01)

(52) U.S. Cl.
CPC .............. *A61N 5/103* (2013.01); *A61B 6/547* (2013.01); *G16H 20/40* (2018.01)

(58) Field of Classification Search
CPC ...... A61N 5/103; A61N 5/1081; A61B 6/547; G16H 20/40
USPC ....................................................... 250/492.3
See application file for complete search history.

(56) References Cited

U.S. PATENT DOCUMENTS

| 7,280,633 B2 | 10/2007 | Cheng et al. |
| 2010/0303205 A1 | 12/2010 | Kapoor et al. |
| 2013/0142310 A1 | 6/2013 | Fahimian et al. |
| 2013/0336449 A1* | 12/2013 | Tanabe ................. A61N 5/1067 378/65 |
| 2019/0209864 A1 | 7/2019 | Stahl et al. |
| 2022/0370833 A1* | 11/2022 | Yonemoto .............. A61N 5/103 |

FOREIGN PATENT DOCUMENTS

| WO | 2015017639 | 2/2015 |
| WO | 2016008052 | 1/2016 |

OTHER PUBLICATIONS

Ye, Beifa et al: "Collision-Free Path Planning and Delivery Sequence Optimization in Noncoplanar Radiation Therapy", IEEE Transactions on Cybernetics, IEEE, Piscataway, NJ, USA, vol. 49, No. 1, Jan. 1, 2019 (Jan. 1, 2019), pp. 42-55.

(Continued)

*Primary Examiner* — Kiet T Nguyen
(74) *Attorney, Agent, or Firm* — Harness, Dickey, & Pierce P.L.C (57) ABSTRACT

Respective target positions, into which elements of a radiation therapy machine are to be moved (e.g., prior to beginning treatment of a patient), are determined. A candidate path, which describes movements of the elements from respective initial positions to the respective target positions, is defined and accessed. The candidate path is evaluated to determine whether it would result in a collision between any of the elements. The candidate path is included in a set of candidate paths when the candidate path does not result in a collision between any of the elements. A value of a measure (e.g., a measure of efficiency), used for ranking each candidate path in the set of candidate paths, is determined. A path is selected from the set of candidate paths based on the ranking.

20 Claims, 6 Drawing Sheets

(56) References Cited

OTHER PUBLICATIONS

Dong, P., Long, T., Ruan, D., Lee, P., Romeijn, D., Low, D., Kupelian, P. and Sheng, K., 2012. 4Pi Radiation therapy for Liver SBRT. International Journal of Radiation Oncology. Biology. Physics, 84(3), p.S202.
Sheng, K., Shepard, D.M. and Orton, C.G., 2015. Noncoplanar beams improve dosimetry quality for extracranial intensity modulated radiotherapy and should be used more extensively. Medical Physics, 42(2), pp. 531-533.
Smyth, G., Evans, P. M., Bamber, J.C. and Bedford, J.L., 2019. Recent developments in non-coplanar radiotherapy. The British journal of radiology, 92(1097), p. 20180908.

* cited by examiner

PATH PLANNING FOR RADIATION TREATMENT

BACKGROUND

The use of radiation therapy to treat cancer is well known. Typically, radiation therapy involves using a radiation therapy machine to deliver a beam of high-energy proton, photon, ion, or electron radiation into a target or target volume (e.g., a volume that includes a tumor or lesion).

Before a patient is treated with radiation, a treatment plan specific to that patient is developed. The plan defines various aspects of the radiation therapy using simulations and optimizations based on past experiences. In general, the purpose of the treatment plan is to deliver sufficient radiation (a prescribed dose) to the unhealthy tissue while minimizing exposure of surrounding healthy tissue to the radiation.

During treatment, the treatment beam is delivered through a treatment head that is attached to a gantry. The treatment head may include, for example, a nozzle for proton or ion beam therapy, a collimator for photon beam therapy, or a collimator with an attached applicator for electron beam therapy. The gantry can be moved to different positions so that the treatment beam can be directed into the target volume at different angles and from different directions. The patient is positioned on a patient support device such as a couch. The patient support can also be moved (e.g., back-and-forth and/or rotated) during treatment so that the patient is at different positions or angles relative to the axis of the treatment beam.

Contemporary radiation therapy machines also include an imaging system for techniques such as image-guided radiation therapy (IGRT). The imaging system is used prior to treatment to position the patient as planned, and may be used during treatment to assess how accurately the treatment plan is being executed.

The gantry, patient support, and imaging system are placed in starting positions before actual treatment begins, and the treatment plan specifies subsequent positions of these elements after treatment begins. The positions and movements of the elements during treatment are preprogrammed into and precisely implemented by a system that controls the radiation therapy machine.

Before actual treatment of the patient can begin, the patient is situated on the patient support and then the gantry, patient support, and imaging system are moved to their starting positions. Placing these elements in their proper starting positions is important for accurate delivery of the radiation when treatment begins. However, moving those elements to their proper starting positions is a time-consuming and manual process that diverts attention away from the patient and requires a high level of training. Each of the elements has multiple degrees of freedom, and so care must be taken to prevent collisions between them and, above all, between them and the patient. Collisions between machine elements and the patient need to be prevented for the sake of patient safety. Collisions between machine elements can cause damage that is costly to repair and can result in postponement of the treatment. Usually, only one element is moved at a time to reduce the likelihood of collisions. Decisions must be made about the order in which the elements are to be moved, and the order that is chosen may not be the most efficient one.

SUMMARY

Embodiments according to the present invention provide a solution to the problems mentioned above. Embodiments according to the present invention provide methods for automatically determining collision-free paths of elements when moving those elements to their starting positions prior to beginning radiation treatment as well as other positions (such as patient unload positions, and positions to set up patient poses), allowing multiple elements to be moved at the same time in a safe and efficient manner. With pre-treatment path plans produced using the disclosed path planning methods, patient safety remains paramount, and the resulting workflow is faster and not prone to human error, delivery times can be reduced, treatment personnel can focus on the patient, and less training of personnel is required, relative to conventional methods.

In embodiments, respective starting positions (hereafter referred to as target positions), into which elements of a radiation therapy machine are to be moved, are determined. The elements include, but are not limited to, the gantry, patient support, and imaging system. In embodiments, a patient surface model is used to represent a volume occupied by a patient on the patient support. The target positions include, for example, the positions of the elements prior to beginning treatment of the patient and other positions used during the workflow (e.g., patient unload positions, and positions to set up patient poses). A candidate path, which describes movements of the elements from their respective initial positions to the respective target positions, is defined and accessed. The candidate path is evaluated to determine whether it would result in a collision between any of the elements, between an element and the modeled patient, and between any of the elements and any other elements of the radiation therapy machine. The candidate path is included in a set of candidate paths when the candidate path does not result in a collision. A value of a measure (e.g., a measure of efficiency), used for ranking each candidate path in the set of candidate paths, is determined. A path for the pre-treatment path plan is selected from the set of candidate paths based on the ranking. Thus, the path that is selected for the path plan is the highest ranked collision-free candidate path.

In other embodiments, a first candidate path is evaluated to determine if it is collision-free and, if so, a measure of efficiency can be determined for that path and the first path is stored in memory. Then, a second candidate path can be evaluated to determine if it is collision-free and, if so, a measure of efficiency can be determined for the second path. If the measure of efficiency of the second candidate path is greater than that of the first candidate path, then the first path is removed from consideration and the second path is stored; otherwise, the first path remains stored as the benchmark against which the next collision-free candidate path is measured. This type of process can be repeated for any number of candidate paths. By the nature of the process, the path that is selected for the pre-treatment path plan will be the highest ranked collision-free candidate path.

In other embodiments, a measure of efficiency is determined for a set of candidate paths before it is determined whether those candidate paths are collision-free. In these embodiments, the candidate paths are ranked from highest to lowest based on their respective measure of efficiency. Then, the highest-ranked candidate path is evaluated to determine whether it is collision-free. If it is, then that candidate path is selected for the path plan; if not, then that path is removed from consideration and the next highest-ranked candidate path is evaluated to determine whether it is collision-free. This type of process is repeated until a collision-free path is found. By this process of elimination, the first collision-free candidate path that is found will be the highest ranked collision-free candidate path.

In other embodiments, an iterative approach is employed to evaluate previously used candidate paths for a new and upcoming treatment. For example, the iterative approach can start with a first set of candidate paths that was safe for a significant number of past treatments, where that set includes paths in which all elements were moved simultaneously (in terms of efficiency, this set would be the highest ranked). If none of those candidate paths is collision-free, then a second and more conservative set of candidate paths (where the second set is ranked lower than the first set in terms of efficiency) that was safe for a significant number of past treatments can be evaluated, and so on.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "executing," "selecting," "applying," "defining," "storing," "dividing," "assigning," "including," "computing," or the like, refer to actions and processes (e.g., the flowcharts of FIGS. 4, 6, and 7) of a computer system or similar electronic computing device or processor (e.g., the computer system 200 of FIG. 2). The computer system or similar electronic computing device manipulates and transforms data represented as physical (electronic) quantities within the computer system memories, registers or other such information storage, transmission or display devices.

Portions of the detailed description that follows are presented and discussed in terms of methods. Although steps and sequencing thereof are disclosed in figures herein (e.g., FIGS. 4, 6, and 7) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Figure 1:
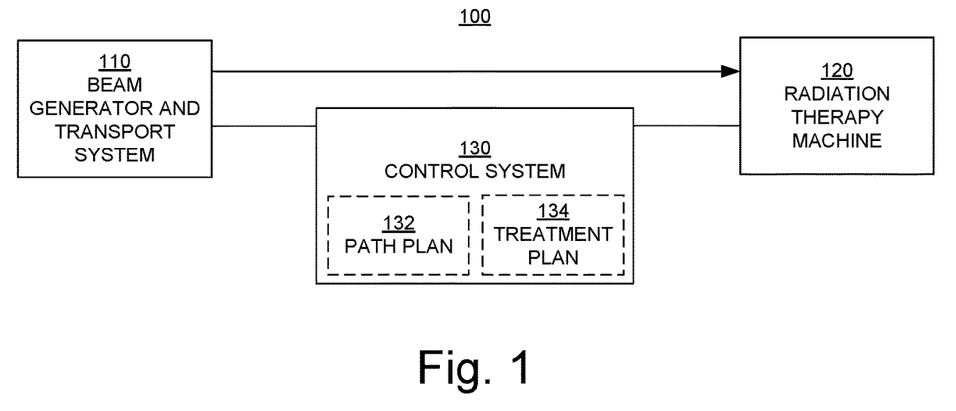
FIG. 1 is a block diagram showing selected elements of an example of a system for radiation therapy in embodiments according to the present invention.

FIG. 1 is a block diagram showing selected elements of an example of a system 100 for radiation therapy in embodiments according to the present invention. In the example of FIG. 1, the system 100 includes a beam generator and transport system 110, a radiation therapy machine 120, and a control system 130. Depending on the type of radiation therapy machine, the beam generator and transport system 110 generates a beam of high-energy proton, photon, ion, or electron radiation, and delivers that beam to the radiation therapy machine 120. The radiation therapy machine 120 in turn delivers the beam into a target volume in a patient (e.g., a volume in the patient that includes a tumor or lesion).

Figure 2:
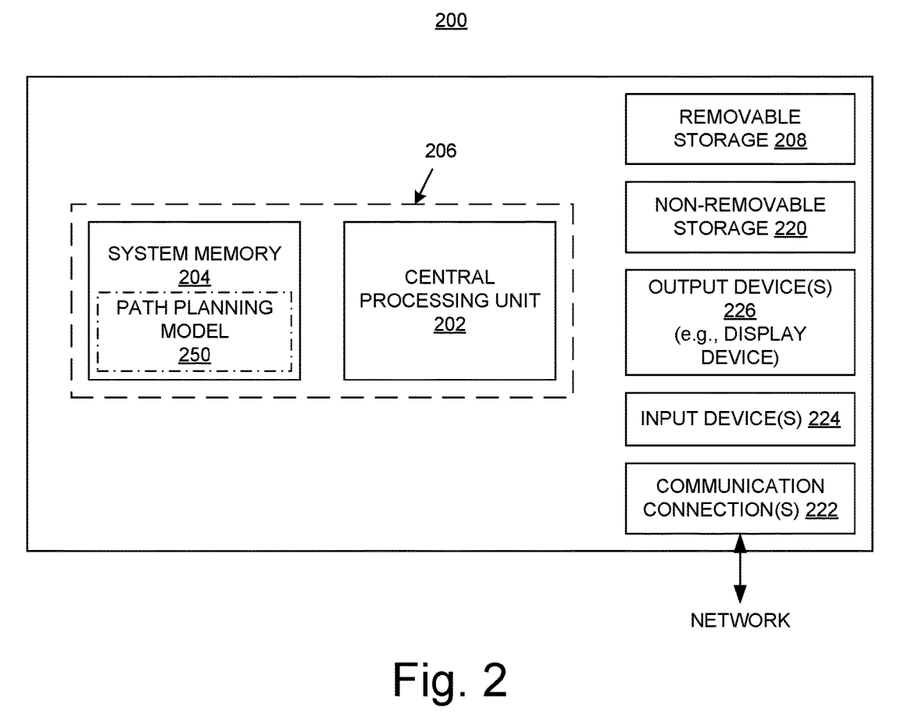
FIG. 2 is a block diagram of an example of a computer system upon which the embodiments described herein may be implemented.
Figure 3A:
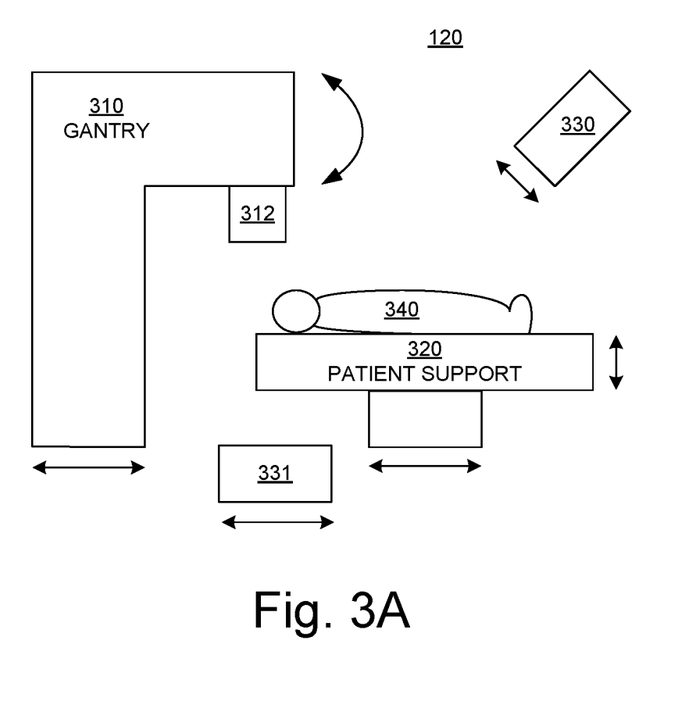
FIGS. 3A and 3B depict elements of examples of radiation therapy machines in embodiments according to the present invention.
Figure 3B:
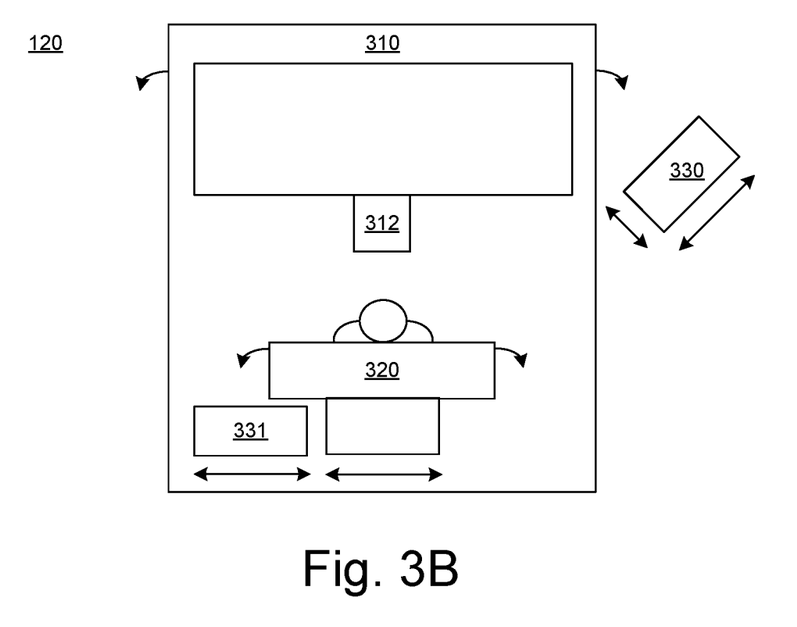

The radiation therapy machine 120 can include elements such as, but not limited to, a gantry, a patient support (e.g., a couch), and an imaging system (see FIGS. 3A and 3B). The control system 130 is used to control the radiation therapy machine 120. More specifically, the control system 130 can include components similar to the computer system 200 of FIG. 2 including, for example, memory that stores a software program as computer-readable and computer-executable instructions and that, when executed, controls movement of the elements such as the gantry, patient support, and imaging system before and during radiation therapy. As will be detailed below, the control system 130 can execute a selected path plan 132 that positions elements such as the gantry, patient support, and imaging system before radiation treatment of a patient begins and during associated workflows (e.g., patient unload positions, and positions to set up patient poses), and can also execute a selected treatment plan 134 that positions those elements during radiation treatment of the patient.

While certain moveable elements have just been identified, embodiments according to the invention are not limited to those elements. Other elements can be moved based on the pre-treatment path plan 132 and/or the treatment plan 134, and the elements moved based on one plan may be different from those moved based on the other plan. For example, the path plan 132 defines movements of external elements of the radiation therapy machine 120, while the treatment plan 134 may define movements of those elements and also may define movements of internal elements (e.g., a collimator) as well as elements of the beam generator and transport system 110.

FIG. 2 shows a block diagram of an example of a computer system 200 upon which the embodiments described herein may be implemented. In its most basic configuration, the system 200 includes at least one processing unit 202 and memory 204. This most basic configuration is illustrated in FIG. 2 by a dashed line 206. The system 200 may also have additional features and/or functionality. For example, the system 200 may also include additional storage (removable and/or non-removable) including, but not limited to, magnetic or optical disks or tape. Such additional storage is illustrated in FIG. 2 by removable storage 208 and non-removable storage 220. The system 200 may also contain communications connection(s) 222 that allow the device to communicate with other devices, e.g., in a networked environment using logical connections to one or more remote computers.

The system 200 also includes input device(s) 224 such as a keyboard, mouse, pen, voice input device, touch input device, etc. Output device(s) 226 such as a display device, speakers, printer, etc., are also included.

In the example of FIG. 2, the memory 204 includes computer-readable and computer-executable instructions, data structures, program modules, and the like associated with a path planning model 250. However, the path planning model 250 may instead reside in any one of the computer storage media used by the system 200, or may be distributed over some combination of the computer storage media, or may be distributed over some combination of networked computers. The path planning model 250 is used to generate the path plan 132 of FIG. 1. The functionality provided by the path planning model 250 is described further below.

As mentioned above, the control system 130 can be implemented using a system like the system 200, but the control system may be implemented on one such system and the path planning model may be implemented on another such system.

FIGS. 3A and 3B depict elements of examples of the radiation therapy machine 120 in embodiments according to the present invention. Only certain elements of the radiation therapy machine 120 are depicted in the examples of FIGS. 3A and 3B. In particular, only selected moveable external elements of the radiation therapy machine 120 are shown. Embodiments according to the present invention are not limited to the depicted elements nor to the depicted examples.

In the examples of FIGS. 3A and 3B, the elements of the radiation therapy machine 120 include: a gantry 310 that includes a treatment head 312; a patient support 320; and an imaging system. The treatment head 312 may include, for example, a nozzle for proton or ion beam therapy, a collimator for photon beam therapy, or a collimator with an attached applicator for electron beam therapy. A patient surface model 340 is used to represent a patient-specific volume occupied by a patient on the patient support 320. The imaging system can be used to create the patient-specific surface model 340.

The imaging system includes an imaging arm or source 330 (e.g., a source of an x-ray beam) and a detector 331. The imaging system may be mounted to the gantry 310. Generally speaking, the source 330 and the detector 331 operate in concert with each other. That is, when the beam from the source 330 is pointed in a different direction, then the position of the detector 331 is also changed so that the detector remains in the path of the beam.

In FIGS. 3A and 3B, the arrows indicate some of the possible axes of motion of the depicted elements. The axes of motion can include rotation about an axis, motion along an axis (e.g., back-and-forth motion), and other types of motion relative to an axis including up-and-down motion and side-to-side motion. The different types of motion (along different axes) can be performed sequentially or at the same time. Although not demonstrated in the figures, the axes of motion can potentially intersect each other. In other words, without proper control as disclosed herein, elements of the radiation therapy machine 120 can collide with one another or with the patient, whose position is not controlled but is accounted for during path planning.

Embodiments according to the present invention provide methods for automatically determining collision-free paths of the elements (axes) including the patient surface model 340, allowing multiple elements to be moved at the same time in a safe and efficient manner. With path plans produced using the disclosed path planning methods, patient safety is paramount but the resulting workflow is faster and not prone to human error, delivery times can be reduced, treatment personnel can focus on the patient, and less training of personnel is required, relative to conventional methods.

Collision-free path planning is a multi-dimensional problem that cannot be practically performed in the human mind. Those dimensions include the multiple elements of the radiation therapy machine 120, their many degrees of freedom, the ranges of movements of those elements, the need for path plans to be not just safe but also efficient, and the time-dependence of the movements (the order of the movements, and the potential for multiple elements to be moved at the same). Consequently, the use of a computer system (e.g., the system 200 of FIG. 2) to consistently and quickly execute the path planning model 250 as disclosed in embodiments herein is important.

Figure 4:
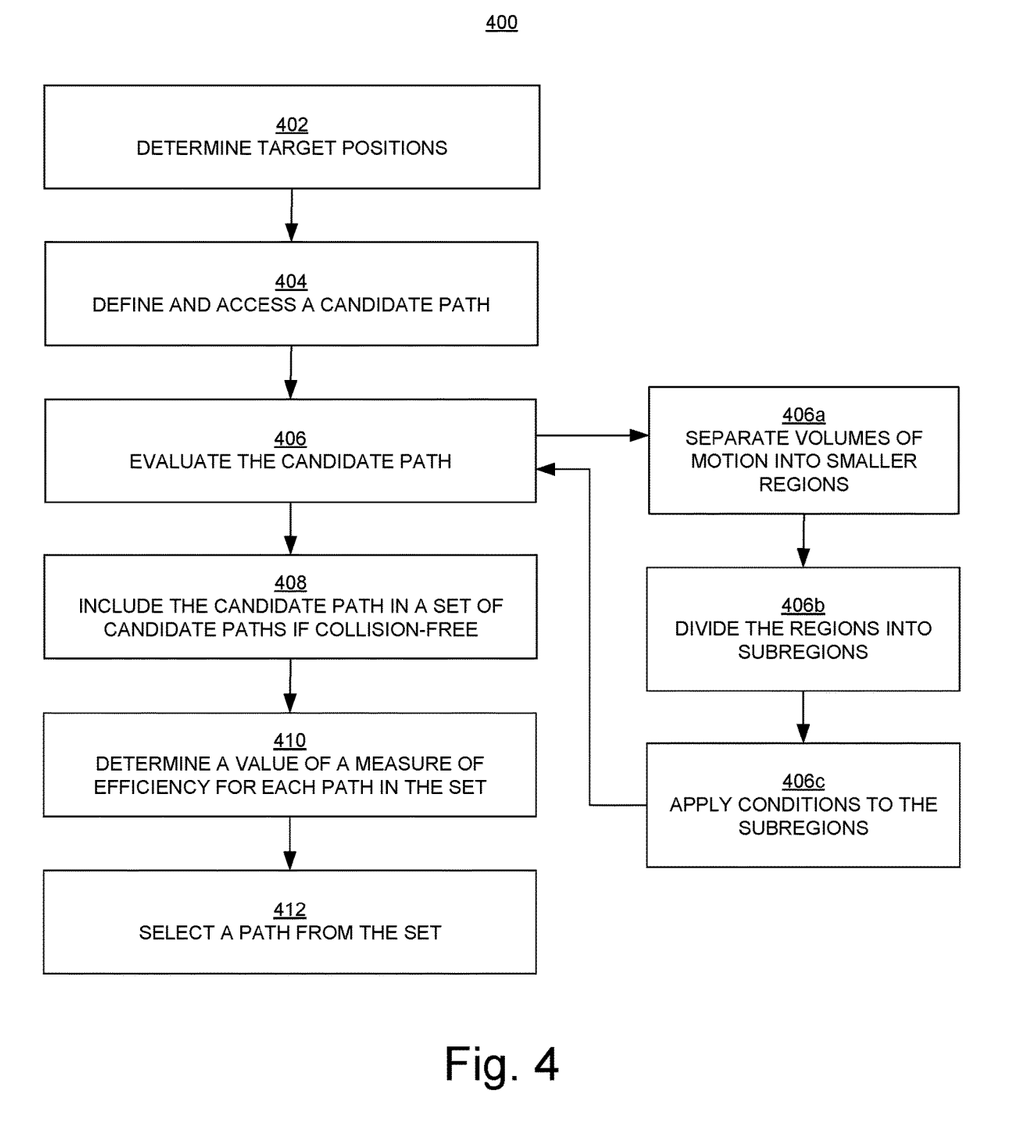
FIG. 4 is a flowchart of examples of computer-implemented operations for path planning in embodiments according to the present invention.

FIG. 4 is a flowchart 400 of examples of computer-implemented operations for path planning in embodiments according to the present invention. The flowchart 400 can be implemented as computer-executable instructions (e.g., the path planning model 250 of FIG. 2) residing on some form of computer-readable storage medium (e.g., a memory of the computer system 200 of FIG. 2).

In overview, in embodiments according to the present invention, path planning includes creating a candidate path, and then checking that path for collisions (safety) and efficiency. The process of creating and checking a candidate path can be an iterative process. A candidate path can be created in different ways, such as by applying heuristics, by geometric optimization, or by machine learning methods. Each candidate path can be checked first for safety, and only then checked for efficiency if it is safe (collision-free). For example, a set of collision-free candidate paths can be created, a measure of efficiency can be determined for each of the collision-free path candidates, and the path candidate ranked the highest according to that measure can be selected as the path that is to be implemented (the path plan 132 of FIG. 1). Measures of efficiency can be based on, for example, the total number of movements or the length of time needed to complete all of the movements. For patient comfort, it may be desirable to minimize the number of times the patient support 320 is moved, and so that factor may be more heavily weighted when determining a measure of efficiency.

FIG. 4 is described with reference also to FIGS. 1, 3A, and 3B. In block 402, respective target positions, into which elements of the radiation therapy machine 120 are to be moved, are determined. The target positions include, for example, the positions of the elements prior to beginning treatment of the patient, positions used during the workflow (e.g., patient unload positions, and positions to set up patient pose). In embodiments, the target positions can be determined based on the radiation treatment plan 134 for the patient to be treated using the radiation therapy machine 120. That is, the radiation treatment plan 134 may specify the target positions for the elements. In an embodiment, the elements include the gantry 310, the imaging system (e.g., the imaging arm or source 330 and the detector 331), the patient support 320, and the patient surface model 340. Embodiments according to the invention are not limited to those elements.

The patient surface model 340 can be determined using computerized tomography, from a point cloud acquired with three-dimensional (3D) cameras, or as a parameterized replacement for a measured model. In embodiments, the patient surface model 340 on the patient support 320 can be treated as a single or integrated element during path planning.

In block 404, a candidate path, which describes movements of the elements from respective initial positions to the respective target positions, is defined and accessed from computer system memory. As noted above, the candidate path can be created using different strategies, such as by applying heuristics, by geometric optimization, or by machine learning methods. The candidate path can also be created using a direct path strategy, in which all of the elements are moved concurrently to the respective target positions. The candidate path can also be created using a 100 percent safe strategy in which the respective initial positions are positions known to provide collision-free paths to the respective target positions.

In block 406, the candidate path is evaluated to determine whether it would result in a collision between any of the elements. In embodiments, a 3D model of the elements of the radiation therapy machine, including the modeled patient, is dynamically adjusted according to movement of any of the elements, and a collision calculation engine is used determine the proximity between any of the elements including the patient.

In embodiments, to perform the evaluation of block 406, the possible spaces or volumes of motion for any axis (moveable element) are divided into smaller characteristic areas (block 406a). In other words, regions of space can be defined for each of the moveable elements, wherein each of the regions of space encompasses possible paths of a respective element of those elements.

In block 406b, in embodiments, those regions of space can, in turn, be divided into subregions. For example, the subregions can be defined based on characteristics such as, but not limited to: the closeness to the center (zero-degree) position of the patient support 320; the amount of rotation of the gantry 310; and the closeness of the gantry position to transition points between upper and lower hemisphere subregions.

Figure 5A:
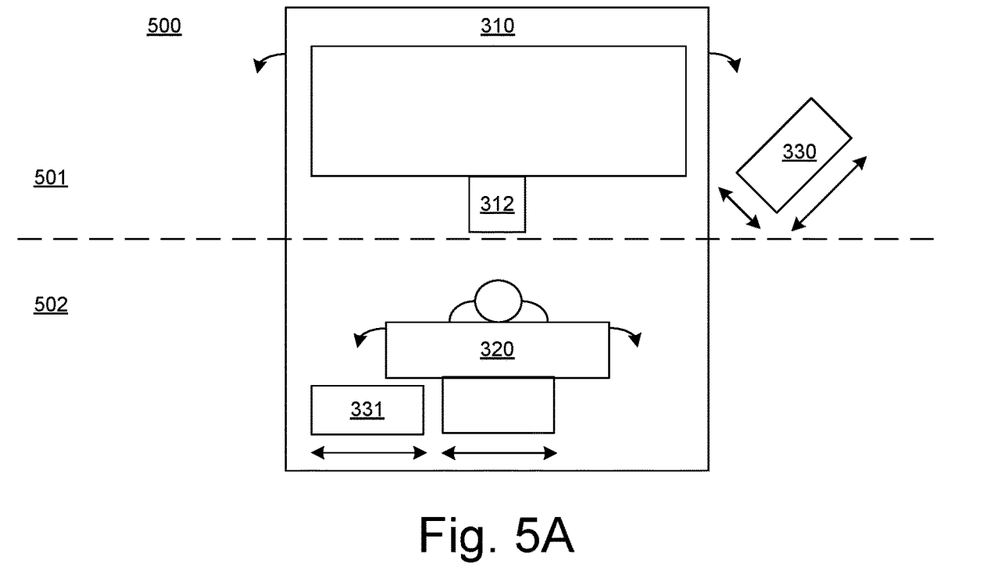
FIGS. 5A and 5B depict elements of examples of radiation therapy machines in embodiments according to the present invention.
Figure 5B:
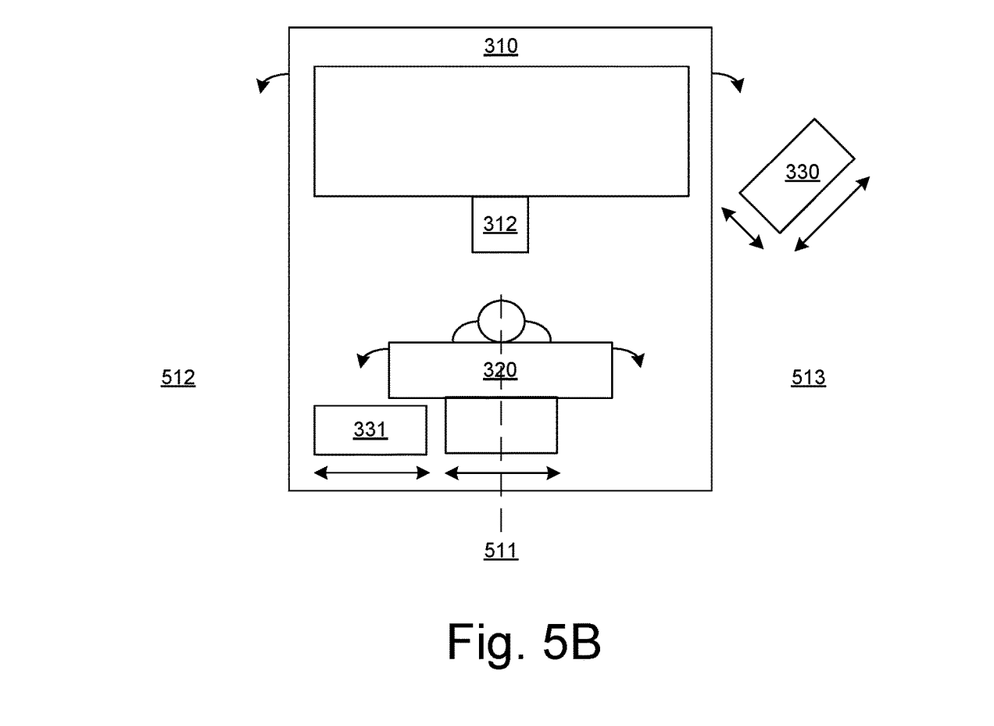

For example, with reference to FIG. 5A, the region 500 within which the gantry 310 can possibly be moved (e.g., rotated) can be divided into an upper hemisphere subregion 501 and a lower hemisphere subregion 502. For example, with reference to FIG. 5B, the region within which the patient support 320 can possibly be moved can be divided into a center subregion 511 and subregions 512 and 513 that are left-of-center and right-of-center, respectively.

In block 406c, in embodiments, conditions that govern movements of the elements within each of the subregions can be applied. For example, a set of conditions can be applied to determine the order in which the elements are moved. The set of conditions can include, but are not limited to:
  if the initial and target positions of the patient support 320 are close to the center 511, then all elements can be moved simultaneously; and
  if the gantry 310 stays in one hemisphere, and neither of the initial or target gantry position are close to a transition point between the hemispheres, then:

if movement of the patient support 320 at both of its initial and target positions is large relative to a defined threshold amount (e.g., 30 degrees from the center), then the patient support needs to be moved first to the center, then the gantry can be moved to its target position, and then the patient support can be moved to its target position;

if movement of the patient support at its initial position is large relative to a defined threshold amount, then the patient support needs to be moved first to its target position, and then the gantry can be moved to its target position; and if movement of the patient support at its target position is large relative to a defined threshold amount, then the gantry needs to be moved first to its target position, and then the patient support can be moved to its target position.

In block 408, the candidate path is included in a set of candidate paths when the candidate path does not result in a collision between any of the selected elements. If the candidate path is not collision-free, it is removed from further consideration (e.g., discarded). All candidate paths in the set are therefore considered to be safe (collision-free). Thus, there is no risk associated with the disclosed method of path planning, as the candidate paths in the set are checked for collisions.

In block 410, a value of a measure (e.g., a measure of efficiency), used for ranking each candidate path in the set of candidate paths, is determined for each path in the set. Measures of efficiency can be based on, for example, the total number of movements or the length of time needed to complete all of the movements. For patient comfort, it may be desirable to minimize the number of times the patient support 320 is moved, and so that factor may be more heavily weighted when determining the measure of efficiency.

Generally speaking, in embodiments, a respective weighting factor can be assigned to each of the moveable elements. For example, if the patient will be in position on the patient support 320 while the elements are being moved to their target positions before treatment begins, then it may be less desirable to move the patient support instead of moving one of the other elements, and so movement of the patient support can be weighted accordingly when determining the measure of efficiency.

In an embodiment, a respective weighting factor is also assigned to each direction of movement of each of the elements. For example, if the patient will be in position on the patient support 320 while the elements are being moved to their target positions before treatment begins, then it may be less desirable to rotate the patient support instead of moving it another way (e.g., back-and-forth) or instead of moving one of the other elements, and so rotation of the patient support can be weighted accordingly when determining the measure of efficiency.

In block 412, a path for the path plan 132 is selected from the set of candidate paths based on the ranking of candidate paths. For example, the candidate path that is highest ranked in terms of efficiency can be selected. Thus, the candidate path that is selected for the path plan 132 is the highest ranked collision-free candidate path.

Alternative path planning approaches that are within the scope of this disclosure are described below.

Figure 6:
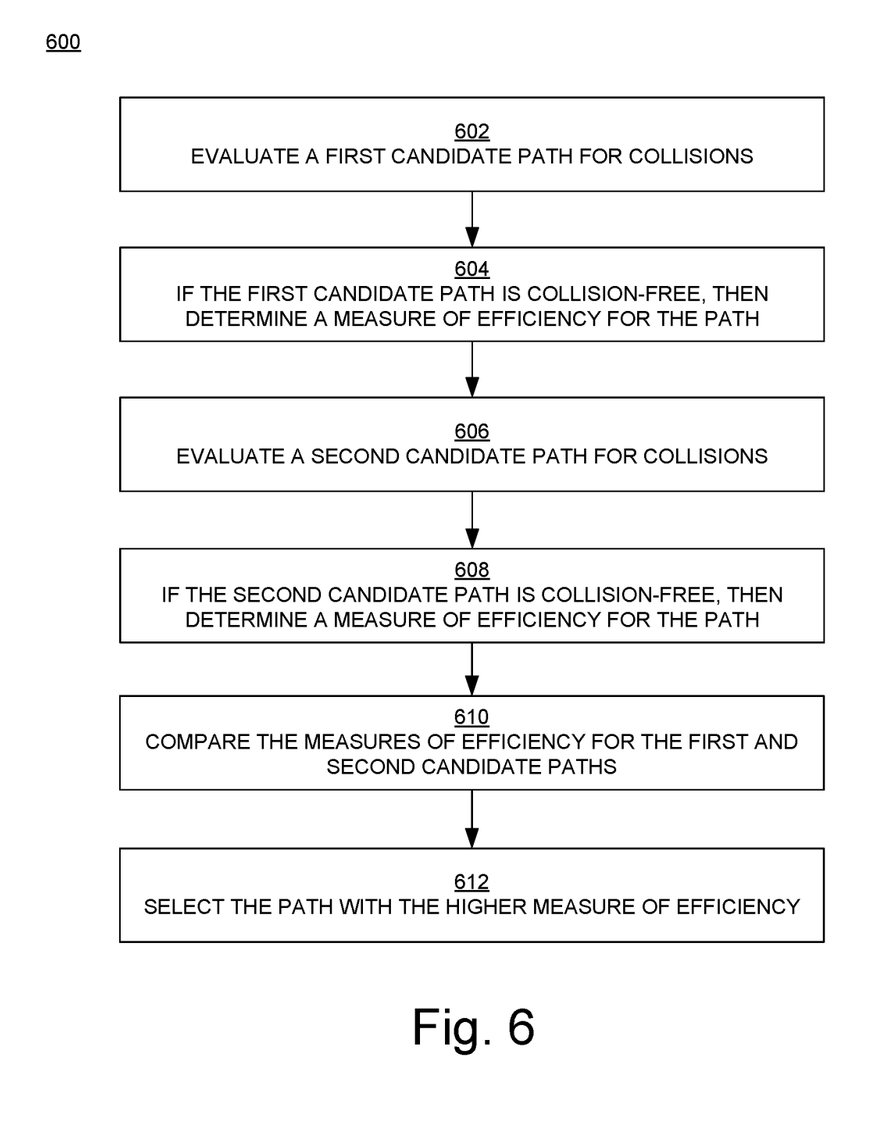
FIG. 6 is a flowchart of examples of computer-implemented operations for path planning in embodiments according to the present invention.

FIG. 6 is a flowchart 600 of examples of computer-implemented operations for path planning in embodiments according to the present invention. The flowchart 600 can be implemented as computer-executable instructions (e.g., the path planning model 250 of FIG. 2) residing on some form of computer-readable storage medium (e.g., a memory of the computer system 200 of FIG. 2).

In block 602 of FIG. 6, a first candidate path is evaluated to determine whether it is collision-free. The first candidate path can be defined, accessed, and evaluated as previously described herein (e.g., see the discussion of FIG. 4).

In block 604 of FIG. 6, if the first candidate path is collision-free, then a measure of efficiency (like that described previously herein) is determined for the first path, and the first path is stored in computer system memory.

In block 606, a second candidate path is evaluated to determine if it is collision-free. The second candidate path can be defined, accessed, and evaluated as previously described herein.

In block 608, if the second candidate path is collision-free, then a measure of efficiency is determined for the second path as previously described herein.

In block 610, the measures of efficiency of the first and second candidate paths are compared.

In block 612, the candidate path with the higher measure of efficiency is selected. More specifically, if the measure of efficiency of the second candidate path is greater than that of the first candidate path, then the first path can be removed from further consideration (e.g., discarded), and the second path is stored in the computer system memory. Otherwise, the first path remains stored as the benchmark against which the next collision-free candidate path is measured.

The operations in the flowchart 600 can be repeated for any number of candidate paths. By the nature of the process, the path selected for the path plan 132 will be the highest ranked collision-free candidate path.

Figure 7:
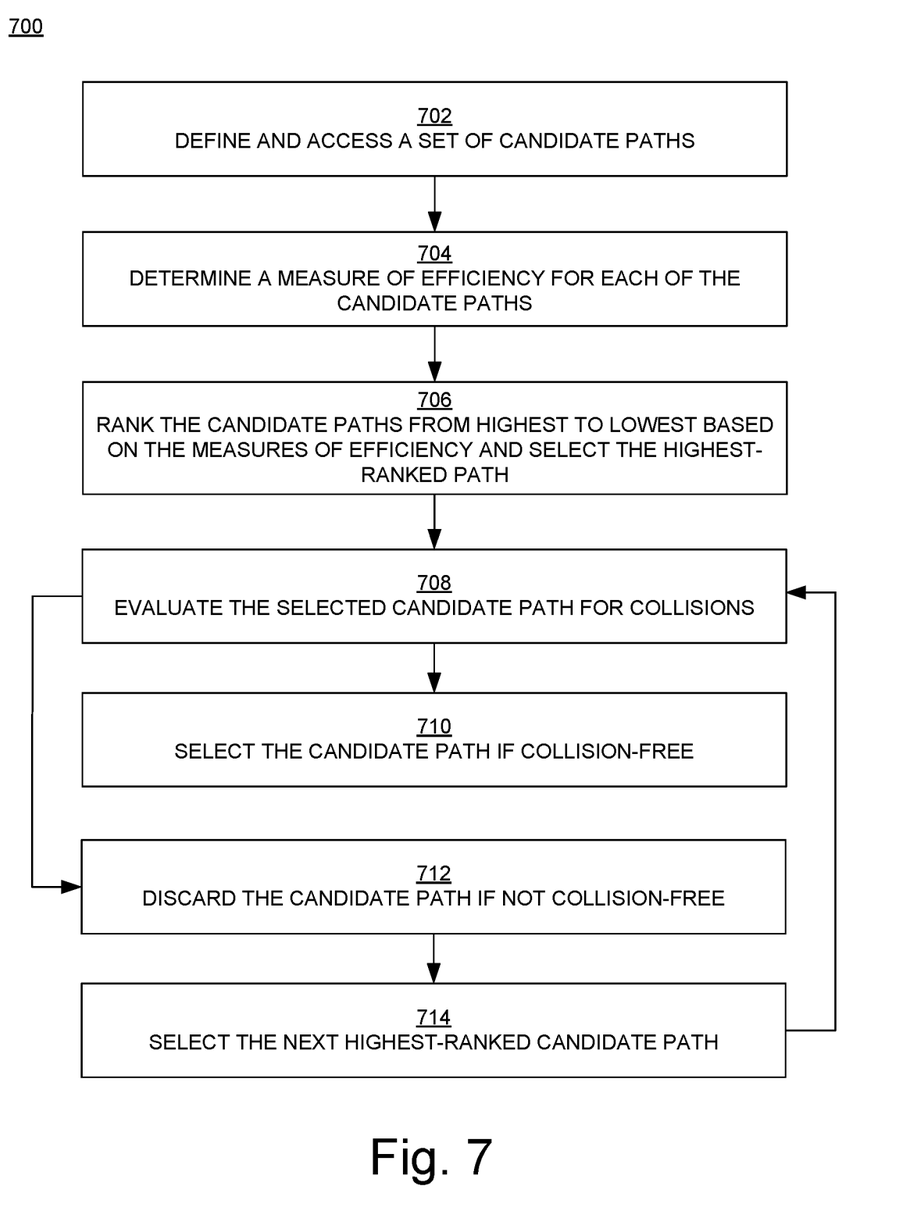
FIG. 7 is a flowchart of examples of computer-implemented operations for path planning in embodiments according to the present invention.

FIG. 7 is a flowchart 700 of examples of computer-implemented operations for path planning in embodiments according to the present invention. The flowchart 700 can be implemented as computer-executable instructions (e.g., the path planning model 250 of FIG. 2) residing on some form of computer-readable storage medium (e.g., a memory of the computer system 200 of FIG. 2).

In block 702 of FIG. 7, a set of candidate paths is defined and accessed. Each of the candidate paths can be defined and accessed as previously described herein (e.g., see the discussion of FIG. 4).

In block 704 of FIG. 7, a measure of efficiency (like that described previously herein) is determined for each candidate path in the set of candidate paths, before it is determined whether the candidate paths are collision-free.

In block 706, the candidate paths are ranked from highest to lowest based on their respective measure of efficiency.

In block 708, the highest-ranked candidate path is evaluated to determine whether it is collision-free.

In block 710, if that candidate path is collision-free, then it is selected for the path plan 132 and the flowchart 700 is concluded; if not, then that path is removed from further consideration (e.g., discarded) (block 712), and the flowchart proceeds to block 714.

In block 714, the next highest-ranked candidate path is selected, and the flowchart 700 returns to block 708, where it is evaluated to determine whether it is collision-free.

The method of FIG. 7 is repeated in the order of ranking until a collision-free path is found. By the process of elimination, the first collision-free path that is found will be the highest ranked collision-free path and can be selected as the path plan 132.

While the operations in FIGS. 4, 6, and 7 are presented as occurring sequentially in a certain order, the present invention is not so limited. The operations may be performed in a different order and/or in parallel, and they may also be performed in an iterative manner.

An iterative approach can be employed to evaluate previously used candidate paths for a new and upcoming treatment. For example, the iterative approach can start with a first set of candidate paths that was safe for a significant number of past treatments, where that set includes paths in which all elements were moved simultaneously (in terms of efficiency, this set would be the highest ranked). If none of those candidate paths is collision-free, then a second and more conservative set of candidate paths (that is, the second set is ranked lower than the first set in terms of efficiency) that was safe for a significant number of past treatments can be evaluated, and so on.

Path plans generated as just described can be used to train a machine learning model that will learn from simulated initial and target positions and a static collision model. The machine learning model can be applied to any arbitrary pair of initial and target positions to find the most efficient and safest path. Many possible scenarios of initial and target positions can be simulated to provide a large training set for training the machine learning model.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
   a processor; and
   memory coupled to the processor and comprising instructions that, when executed, cause the processor to execute operations for a method of path planning for a radiation therapy machine, the operations comprising:
   determining respective target positions into which a plurality of elements of the radiation therapy machine are to be moved;
   accessing a candidate path that describes movements of the elements from respective initial positions to the respective target positions;
   determining whether the candidate path would result in a collision between any element of the plurality of elements;
   including the candidate path in a set of candidate paths when the candidate path does not result in a collision between any element of the plurality of elements; and
   selecting a path from the set of candidate paths.

2. The computer system of claim 1, wherein the set of candidate paths also includes a candidate path in which all elements of the plurality of elements are moved concurrently to the respective target positions.

3. The computer system of claim 1, wherein the set of candidate paths also includes a candidate path in which the respective initial positions are positions known to provide collision-free paths to the respective target positions.

4. The computer system of claim 1, wherein the method further comprises determining a value of a measure used for ranking each candidate path in the set of candidate paths; wherein said selecting comprises selecting a path from the set of candidate paths based on the ranking.

5. The computer system of claim 1, wherein said determining whether the candidate path would result in a collision between any element of the plurality of elements comprises:
   defining regions of space for each element of the plurality of elements, wherein each of the regions of space encompasses possible paths of a respective element of the elements;
   dividing each of the regions into subregions; and
   applying conditions that govern movements of the elements within each of the subregions.

6. The computer system of claim 1, wherein the plurality of elements of the radiation therapy machine comprises a gantry, an imaging arm, and a patient support.

7. The computer system of claim 1, wherein the plurality of elements comprises a model of a patient disposed on a patient support.

8. The computer system of claim 1, wherein a respective weighting factor is assigned to each direction of movement of each element of the plurality of elements.

9. The computer system of claim 1, wherein a respective weighting factor is assigned to each element of the plurality of elements.

10. A computer-implemented method of path planning for a radiation therapy machine, the method comprising:
    determining respective target positions into which a plurality of elements of the radiation therapy machine are to be moved;
    accessing a candidate path comprising a description of movements of the plurality of elements from respective initial positions of the plurality of elements to the respective target positions;
    determining whether the candidate path would result in a collision between any element of the plurality of elements;
    including the candidate path in a set of candidate paths when the candidate path does not result in a collision between any element of the plurality of elements; and
    selecting a path from the set of candidate paths.

11. The method of claim 10, further comprising determining a value of a measure used for ranking each candidate path in the set of candidate paths;
    wherein said selecting comprises selecting a candidate path from the set of candidate paths based on the ranking.

12. The method of claim 10, further comprising:
    defining regions of space for each element of the plurality of elements, wherein each of the regions of space encompasses possible paths of a respective element of the elements;
    dividing each of the regions into subregions; and
    applying conditions that govern movements of the elements within each of the subregions.

13. The method of claim 10, wherein the plurality of elements of the radiation therapy machine comprises a gantry, an imaging arm, and a patient support.

14. The method of claim 10, wherein the plurality of elements comprises a model of a patient disposed on a patient support.

15. The method of claim 10, wherein a respective weighting factor is assigned to each direction of movement of each element of the plurality of elements, and wherein a respective weighting factor is assigned to each element of the plurality of elements.

16. A non-transitory computer-readable storage medium having computer-executable instructions for causing a computer system to perform a method of path planning for a radiation therapy machine, the method comprising:
    determining respective target positions into which a plurality of elements of the radiation therapy machine are to be moved;

accessing a candidate path comprising a description of movements of the elements from respective initial positions of the elements to the respective target positions;

determining whether the candidate path would result in a collision between any element of the plurality of elements;

including the candidate path in a set of candidate paths when the candidate path does not result in a collision between any element of the plurality of elements; and selecting a path from the set of candidate paths.

17. The non-transitory computer-readable storage medium of claim 16, wherein the method further comprises determining a value of a measure used for ranking each candidate path in the set of candidate paths;

wherein said selecting comprises selecting a path from the set of candidate paths based on the ranking.

18. The non-transitory computer-readable storage medium of claim 16, wherein the method further comprises:

defining regions of space for each element of the plurality of elements, wherein each of the regions of space encompasses possible paths of a respective element of the plurality of elements;

dividing each of the regions into subregions; and applying conditions that govern movements of the elements within each of the subregions.

19. The non-transitory computer-readable storage medium of claim 16, wherein the plurality of elements of the radiation therapy machine comprises a gantry, an imaging arm, a patient support, and a model of a patient disposed on the patient support.

20. The non-transitory computer-readable storage medium of claim 16, wherein a respective weighting factor is assigned to each direction of movement of each element of the plurality of elements, and wherein a respective weighting factor is assigned to each element of the plurality of elements.

* * * * *